(12) United States Patent
Kwok et al.

(10) Patent No.: US 7,243,651 B2
(45) Date of Patent: *Jul. 17, 2007

(54) CUSHION AND MASK THEREFOR

(75) Inventors: Philip Rodney Kwok, West Pymble (AU); Robert Edward Styles, Glenhaven (AU)

(73) Assignee: ResMed Limited, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/934,402

(22) Filed: Sep. 7, 2004

(65) Prior Publication Data

US 2005/0022818 A1   Feb. 3, 2005

Related U.S. Application Data

(60) Continuation of application No. 10/004,428, filed on Dec. 6, 2001, now Pat. No. 6,871,649, which is a division of application No. 09/566,806, filed on May 8, 2000, now Pat. No. 6,634,358, which is a continuation of application No. 08/791,212, filed on Jan. 31, 1997, now Pat. No. 6,112,746.

(30) Foreign Application Priority Data

Jul. 26, 1996   (AU) .................... PO1265

(51) Int. Cl.
*A62B 18/02* (2006.01)
*A62B 18/08* (2006.01)

(52) U.S. Cl. ............... 128/205.25; 128/206.24
(58) Field of Classification Search ......... 128/205.25, 128/206.24, 207.11
See application file for complete search history.

(56) References Cited

U.S. PATENT DOCUMENTS 781,516 A   1/1905   Guthrie (Continued)

FOREIGN PATENT DOCUMENTS

AU   64058/86   4/1987

(Continued)

OTHER PUBLICATIONS

Japanese Office Action and Translation for Application No. 508323/1998, Mailed Jul. 1, 2003 (6 pages).

(Continued)

*Primary Examiner*—Justine R. Yu
*Assistant Examiner*—Kristen C Matter
(74) *Attorney, Agent, or Firm*—Nixon & Vanderhye P.C.

(57) ABSTRACT

A nasal cushion (30) comprises a substantially triangularly shaped frame (32) from which extends a membrane (34). The frame (32) has a scalloped edge (36) by which the cushion (30) is affixed to a mask body. The membrane (34) has an aperture (38) into which the wearer's nose is received. The membrane (34) is spaced away from the rim (40) of the frame (32), and its outer surface (41) is of substantially the same shape as the rim (40). Respective notches (42,44) receive the bridge of the wearer's nose. The wearer's nose is received through the aperture (38) into the chamber within the mask body (46). The seal forming portion (45) thus contacts both the surface of the wearer's nose and a portion of the wearer's face in the region between the base of the nose and the upper lip, and around the sides and over the bridge of the nose. The shape of the seal forming portion (45) is particularly suited to effectively seal the difficult region of the facial contour that is the crease between the sides of the nose and the face.

29 Claims, 3 Drawing Sheets

U.S. PATENT DOCUMENTS

| | | | |
|---|---|---|---|
| 812,706 A | 2/1906 | Warbasse | |
| 902,961 A * | 11/1908 | Goodnow | 128/207.11 |
| 1,000,706 A * | 8/1911 | Barnum | 128/206.28 |
| 1,081,745 A | 12/1913 | Johnston et al. | |
| 1,105,127 A | 7/1914 | Drager | |
| 1,192,186 A | 7/1916 | Greene | |
| 1,632,449 A | 6/1927 | McKesson | |
| 1,653,572 A | 12/1927 | Jackson | |
| 1,926,027 A | 9/1933 | Biggs | |
| 2,123,353 A | 7/1938 | Catt | |
| 2,166,164 A | 7/1939 | Lemberg | |
| 2,248,477 A | 7/1941 | Lombard | |
| 2,254,854 A | 9/1941 | O'Connell | |
| 2,317,608 A | 4/1943 | Heidbrink | |
| 2,371,965 A | 3/1945 | Lemberg | |
| 2,376,871 A | 5/1945 | Fink | |
| 2,415,846 A | 2/1947 | Randall | |
| 2,438,058 A | 3/1948 | Kincheloe | |
| 2,578,621 A | 12/1951 | Yant | |
| 2,625,155 A | 1/1953 | Engelder | |
| 2,710,602 A | 6/1955 | Maybach | |
| 2,875,757 A | 3/1959 | Galleher, Jr. | |
| 2,931,356 A | 4/1960 | Schwarz | |
| D188,084 S | 5/1960 | Garelick | |
| 2,939,458 A | 6/1960 | Lundquist | |
| 3,013,556 A | 12/1961 | Galleher | |
| 3,044,464 A | 7/1962 | Gray | |
| 3,182,659 A | 5/1965 | Blount et al. | |
| 3,189,027 A | 6/1965 | Bartlett | |
| 3,193,624 A | 7/1965 | Webb et al. | |
| 3,238,943 A | 3/1966 | Holley | |
| 3,315,674 A | 4/1967 | Bloom et al. | |
| 3,330,273 A | 7/1967 | Bennett | |
| 3,330,274 A | 7/1967 | Bennett | |
| 3,362,420 A | 1/1968 | Blackburn et al. | |
| 3,363,833 A | 1/1968 | Laerdal | |
| 3,556,122 A | 1/1971 | Laerdal | |
| 3,580,051 A | 5/1971 | Blevins | |
| 3,700,000 A | 10/1972 | Hesse et al. | |
| 3,720,235 A | 3/1973 | Schrock | |
| 3,725,953 A | 4/1973 | Johnson et al. | |
| 3,796,216 A | 3/1974 | Schwarz | |
| 3,799,164 A | 3/1974 | Rollins | |
| D231,803 S | 6/1974 | Huddy | |
| 4,077,404 A | 3/1978 | Elam | |
| D250,131 S | 10/1978 | Lewis et al. | |
| 4,167,185 A | 9/1979 | Lewis | |
| 4,226,234 A | 10/1980 | Gunderson | |
| 4,245,632 A | 1/1981 | Houston | |
| D262,322 S | 12/1981 | Mizerak | |
| 4,304,229 A | 12/1981 | Curtin | |
| 4,305,387 A | 12/1981 | Reist-Kundig et al. | |
| 4,328,797 A | 5/1982 | Rollins et al. | |
| 4,347,205 A | 8/1982 | Stewart | |
| 4,354,488 A | 10/1982 | Bartos | |
| 4,402,316 A | 9/1983 | Gadberry | |
| 4,412,537 A | 11/1983 | Tiger | |
| 4,467,799 A | 8/1984 | Steinberg | |
| 4,522,639 A | 6/1985 | Ansite et al. | |
| 4,558,710 A | 12/1985 | Eichler | |
| 4,616,647 A | 10/1986 | McCreadie | |
| 4,622,964 A | 11/1986 | Flynn | |
| 4,655,213 A | 4/1987 | Rappaport et al. | |
| 4,658,763 A | 4/1987 | Gobien et al. | |
| 4,665,570 A | 5/1987 | Davis | |
| 4,671,271 A | 6/1987 | Bishop et al. | |
| 4,677,975 A | 7/1987 | Edgar et al. | |
| 4,677,977 A | 7/1987 | Wilcox | |
| 4,699,092 A | 10/1987 | Ruf et al. | |
| D293,613 S | 1/1988 | Wingler | |
| 4,739,755 A * | 4/1988 | White et al. | 128/206.12 |
| 4,770,169 A | 9/1988 | Schmoegner et al. | |
| 4,774,941 A | 10/1988 | Cook | |
| 4,782,832 A | 11/1988 | Trimble et al. | |
| 4,799,477 A | 1/1989 | Lewis | |
| 4,803,981 A | 2/1989 | Vickery | |
| 4,809,692 A | 3/1989 | Nowacki et al. | |
| 4,811,730 A | 3/1989 | Milano | |
| 4,819,629 A | 4/1989 | Jonson | |
| 4,821,713 A | 4/1989 | Bauman | |
| 4,841,953 A | 6/1989 | Dodrill | |
| 4,848,334 A | 7/1989 | Belim | |
| 4,848,366 A | 7/1989 | Alta et al. | |
| 4,889,079 A | 12/1989 | Takeda et al. | |
| 4,907,584 A | 3/1990 | McGinnis | |
| 4,910,806 A | 3/1990 | Baker et al. | |
| 4,919,128 A | 4/1990 | Kopala et al. | |
| 4,922,921 A | 5/1990 | Donoghue | |
| 4,938,210 A | 7/1990 | Shene | |
| 4,938,212 A | 7/1990 | Gnook et al. | |
| 4,944,310 A | 7/1990 | Sullivan | |
| D310,431 S | 9/1990 | Belim | |
| 4,971,051 A | 11/1990 | Toffolon | |
| 4,986,269 A | 1/1991 | Hakkinen | |
| 4,989,596 A | 2/1991 | Macris et al. | |
| 4,989,599 A | 2/1991 | Carter | |
| 5,003,633 A | 4/1991 | Itoh | |
| 5,005,568 A | 4/1991 | Loescher et al. | |
| 5,005,571 A | 4/1991 | Dietz | |
| 5,038,776 A | 8/1991 | Harrison et al. | |
| 5,042,473 A | 8/1991 | Lewis | |
| 5,042,478 A | 8/1991 | Kopala et al. | |
| 5,046,200 A | 9/1991 | Feder | |
| 5,063,922 A | 11/1991 | Hakkinen | |
| 5,065,756 A * | 11/1991 | Rapoport | 128/204.18 |
| 5,069,205 A | 12/1991 | Urso | |
| D323,908 S | 2/1992 | Hollister et al. | |
| 5,094,193 A | 3/1992 | Yoshikawa | |
| 5,109,839 A | 5/1992 | Blasdell et al. | |
| 5,109,840 A | 5/1992 | Daleiden | |
| 5,121,745 A | 6/1992 | Israel | |
| 5,133,347 A | 7/1992 | Huennenbeck | |
| 5,140,980 A | 8/1992 | Haughey et al. | |
| 5,140,982 A | 8/1992 | Bauman | |
| 5,148,802 A * | 9/1992 | Sanders et al. | 128/204.18 |
| 5,159,938 A | 11/1992 | Laughlin | |
| 5,178,138 A | 1/1993 | Walstrom et al. | |
| D334,633 S | 4/1993 | Rudolph | |
| 5,231,983 A | 8/1993 | Matson et al. | |
| 5,233,978 A | 8/1993 | Callaway | |
| 5,243,971 A | 9/1993 | Sullivan et al. | |
| 5,265,595 A | 11/1993 | Rudolph | |
| 5,279,289 A | 1/1994 | Kirk | |
| 5,280,784 A | 1/1994 | Kohler | |
| 5,311,862 A | 5/1994 | Blasdell et al. | |
| 5,322,057 A | 6/1994 | Raabe et al. | |
| 5,343,878 A | 9/1994 | Scarberry et al. | |
| 5,349,949 A | 9/1994 | Schegerin | |
| 5,357,951 A | 10/1994 | Ratner | |
| 5,372,130 A | 12/1994 | Stern et al. | |
| 5,388,571 A | 2/1995 | Roberts et al. | |
| 5,404,871 A | 4/1995 | Goodman et al. | |
| 5,419,318 A | 5/1995 | Tayebi | |
| 5,429,126 A | 7/1995 | Bracken | |
| 5,429,683 A | 7/1995 | Le Mitouard | |
| 5,431,158 A | 7/1995 | Tirotta | |
| 5,438,981 A | 8/1995 | Starr et al. | |
| 5,441,046 A | 8/1995 | Starr et al. | |
| D362,061 S | 9/1995 | McGinnis et al. | |
| 5,477,852 A | 12/1995 | Landis et al. | |
| 5,479,920 A | 1/1996 | Piper et al. | |
| 5,488,948 A | 2/1996 | Dubruille et al. | |
| 5,492,116 A | 2/1996 | Scarberry et al. | |
| 5,501,214 A | 3/1996 | Sabo | |

| | | | |
|---|---|---|---|
| 5,509,404 A | 4/1996 | Lloyd et al. | |
| 5,517,986 A * | 5/1996 | Starr et al. ............ 128/206.24 | |
| 5,538,000 A | 7/1996 | Rudolph | |
| 5,540,223 A | 7/1996 | Starr et al. | |
| 5,542,128 A | 8/1996 | Lomas | |
| 5,546,936 A | 8/1996 | Virag et al. | |
| RE35,339 E | 10/1996 | Rappaport | |
| 5,560,354 A | 10/1996 | Berthon-Jones et al. | |
| 5,570,682 A | 11/1996 | Johnson | |
| 5,570,689 A | 11/1996 | Starr et al. | |
| D377,089 S | 12/1996 | Starr et al. | |
| 5,592,938 A | 1/1997 | Scarberry et al. | |
| 5,608,647 A | 3/1997 | Rubsamen et al. | |
| 5,642,730 A | 7/1997 | Baran | |
| 5,647,355 A | 7/1997 | Starr et al. | |
| 5,647,357 A | 7/1997 | Barnett et al. | |
| 5,649,532 A | 7/1997 | Griffiths | |
| 5,649,533 A | 7/1997 | Oren | |
| 5,655,520 A | 8/1997 | Howe et al. | |
| 5,657,493 A | 8/1997 | Ferrero et al. | |
| 5,657,752 A | 8/1997 | Landis et al. | |
| 5,660,174 A | 8/1997 | Jacobelli | |
| 5,662,101 A | 9/1997 | Ogden et al. | |
| 5,666,946 A | 9/1997 | Langenback | |
| 5,685,296 A | 11/1997 | Zdrojkowski et al. | |
| 5,687,715 A | 11/1997 | Landis et al. | |
| 5,715,814 A | 2/1998 | Ebers | |
| 5,746,201 A | 5/1998 | Kidd | |
| 5,813,423 A | 9/1998 | Kirchgeorg | |
| 5,832,918 A | 11/1998 | Pantino | |
| 5,884,624 A | 3/1999 | Barnett et al. | |
| 6,082,360 A | 7/2000 | Rudolph et al. | |
| 6,102,040 A | 8/2000 | Tayebi et al. | |
| 6,112,746 A * | 9/2000 | Kwok et al. ............ 128/207.13 | |
| 6,412,487 B1 | 7/2002 | Gunaratnam et al. | |
| 6,581,602 B2 | 6/2003 | Kwok et al. | |
| 6,634,358 B2 * | 10/2003 | Kwok et al. ............ 128/205.25 | |
| 6,701,927 B2 | 3/2004 | Kwok et al. | |
| 6,871,649 B2 * | 3/2005 | Kwok et al. ............ 128/206.24 | |
| 7,007,696 B2 * | 3/2006 | Palkon et al. .......... 128/207.13 | |
| 2002/0104540 A1 | 8/2002 | Kwok et al. | |

FOREIGN PATENT DOCUMENTS

| | | |
|---|---|---|
| AU | 91/77110 B | 11/1991 |
| AU | 94/64816 B | 12/1994 |
| AU | 95/16178 B | 7/1995 |
| AU | 9459430 | 2/1996 |
| AU | A 32914/95 | 2/1996 |
| AU | A 41018/97 | 4/1998 |
| AU | A 89312/98 | 1/1999 |
| CA | 1039144 | 9/1998 |
| DE | 459104 | 4/1928 |
| DE | 701 690 | 1/1941 |
| DE | 159396 | 6/1981 |
| DE | 3015279 A1 | 10/1981 |
| DE | 3345067 A1 | 6/1984 |
| DE | 3537507 A1 | 4/1987 |
| DE | 3539073 A1 | 5/1987 |
| DE | 4004157 C1 | 4/1991 |
| DE | 4343205 A1 | 6/1995 |
| DE | 19548 380 A1 | 12/1995 |
| DE | 195 48 380 A1 | 7/1996 |
| DE | 197 35 359 | 1/1998 |
| DE | 297 23 101 | 7/1998 |
| DE | 298 10846 U1 | 8/1998 |
| EP | 0 054 154 | 10/1981 |
| EP | 0 252 052 | 7/1987 |
| EP | 0 264 772 | 10/1987 |
| EP | 0 252 052 | 1/1988 |
| EP | 0 264 772 | 4/1988 |
| EP | 0 303 090 B1 | 7/1988 |
| EP | 303 090 B1 | 7/1988 |
| EP | 0 386 605 A1 | 2/1990 |
| EP | 0 462 701 A1 | 5/1991 |
| EP | 0427474 A2 | 5/1991 |
| EP | 0 462 701 | 12/1991 |
| EP | 0634186 A2 | 6/1993 |
| EP | 0 602 424 | 11/1993 |
| EP | 0 634 186 A2 | 6/1994 |
| EP | 0608 84 A1 | 8/1994 |
| EP | 178 925 A2 | 4/1996 |
| EP | 0 747 078 | 12/1996 |
| EP | 0 747 078 A2 | 12/1996 |
| EP | 0821 978 | 2/1998 |
| FR | 801629 | 8/1936 |
| FR | 858749 | 12/1940 |
| FR | 2 254 657 A1 | 6/1986 |
| FR | 2 658 725 A1 | 8/1991 |
| FR | 2 749 176 | 12/1997 |
| GB | 775911 | 5/1957 |
| GB | 1395391 | 5/1975 |
| GB | 1 467 828 | 3/1977 |
| GB | 2145335 A | 3/1985 |
| GB | 2147506 A | 5/1985 |
| GB | 2 164 569 A | 3/1986 |
| GB | 2211098 A | 6/1989 |
| GB | 2267 648 A | 12/1993 |
| IT | 326983 | 6/1935 |
| JP | 44-16955 | 7/1969 |
| JP | 09/216240 A | 8/1997 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO94/02190 | 2/1994 |
| WO | WO 94/16759 | 8/1994 |
| WO | WO 94/19055 | 9/1994 |
| WO | WO 94/20051 | 9/1994 |
| WO | WO 95/02428 | 1/1995 |
| WO | 0 697 225 | 7/1995 |
| WO | WO 96/17643 | 6/1996 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/48878 | 11/1998 |

OTHER PUBLICATIONS

Respironics, Inc. "Nasal Mask and Accessories Guide," Dec. 23, 1991, 6 pages.

"InterVENTions, A Ventilatory Care Newsletter," vol. 93, No. 1, Mar. 1993, Respironics, Inc., 16 pages.

"Order" from *Respironics, Inc.* v. *ResCare Limited et al.* case, Civil Action No. 95-151, with Exhibits E and G related to information allegedly available before Jul. 26, 1995, 20 pages+.

Instructions for Use for the Comfort Flap Small Child Contour Nasal Mask Accessory, Respironics Inc., Jul. 19, 1993, 2 pages.

"Comfort Flap™ Improves the Seal on Reusable Contour Nasal masks," InterVENTions, vol. 3 No. 1, Mar. 1993, 2 pages.

Mask 1 photographs, Respironics, Inc., Reusable Full mask (small) Part # 452033 lot # 951108.

Mask 2 Photographs, Puritain-Bennett, Adam Circuit, Shell part # 231700, Swivel part # 616329-00, Pillows (medium) Part # 616324.

Mask 3 Photographs, DeVilbiss Healthcare Inc., DeVilbiss Seal-ring and CPAP Mask Kit (medium) Part 73510-669.

Mask 4 Photographs, Respironics, Inc., onarch Mini Mask With Pressure Port, part #572004.Monarch Headgear, Part # 572011.

Mask 5 Photographs, Healthdyne Technologies, Nasal CPAP Mask (medium narrow), part # 702510.

Mask 6 Photographs, Healthdyne Technologies, Soft Series Nasal CPAP Mask, part 3702020.

Mask 7 Photographs, DeVilbiss Healthcare, Inc., Small mask and Seal Rings, part # 73510-668.

Mask 8 Photographs, Respironics, Inc., REUSABLE Contour mask (medium), part # 302180.

Mask 9 Photographs, Healthdyne Technologies, Healthdyne Large Headgear.

Mask 10 Photographs, Respironics, inc., Soft cap (medium), Part #302142.

Mask 11 Photographs, Weinmann: Hamburg, Nasalmaskensystem Mit Schalldämpfer (medium), Part # WN 23105.

Mask 12 Photographs, Life Care.

Mask 13 Photographs, Healthdyne Technologies.

Mask 14, King System.

Mask 15 Photographs, Respironics, Inc., Paediatric Mask.

Mask 16 Photographs, Hans Rudolph Inc., Hans Rudolph Silicone Rubber Face Mask/8900.

* cited by examiner

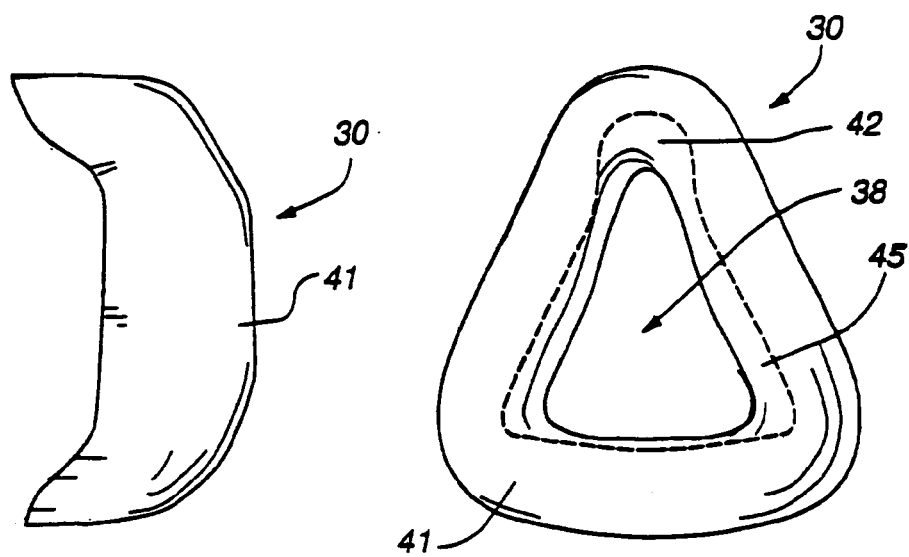
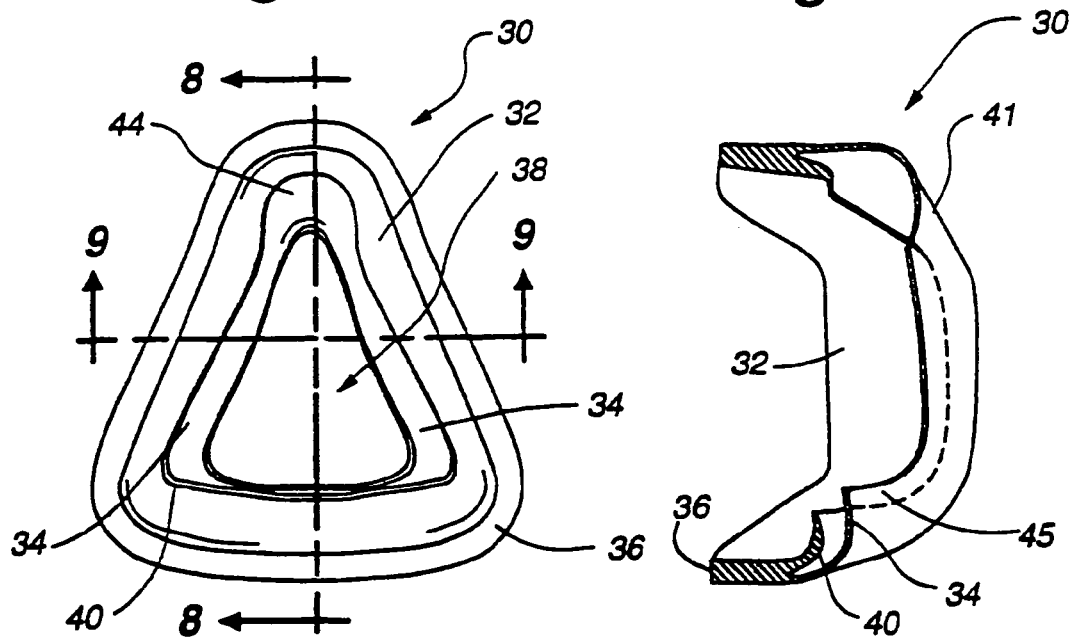
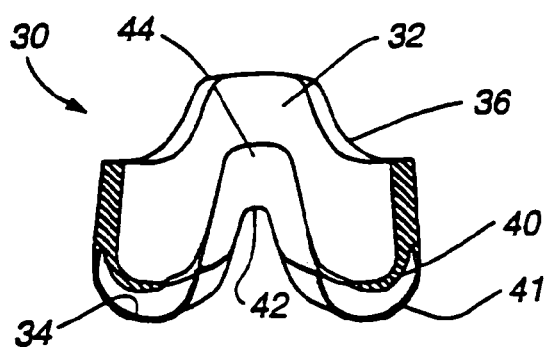

CUSHION AND MASK THEREFOR

CROSS REFERENCE TO RELATED APPLICATIONS

This application is a continuation of U.S. application Ser. No. 10/004,428, filed Dec. 6, 2001 now U.S. Pat. No. 6,871,649, now allowed, which is a divisional of U.S. application Ser. No. 09/566,806, filed May 8, 2000, now U.S. Pat. No. 6,634,358, which is a continuation of U.S. application Ser. No. 08/791,212, filed Jan. 31, 1997, now U.S. Pat. No. 6,112,746, the contents of which are incorporated by reference herein in their entireties.

FIELD OF THE INVENTION

The invention relates generally to a nasal mask and to a cushion therefor, for example, for use in the treatment of respiratory conditions and in assisted respiration.

BACKGROUND OF THE INVENTION

Nasal masks are commonly used in the treatment of respiratory conditions and sleep disorders (e.g., obstructive sleep apnea) by delivering a flow of breathable gas for, or to assist patient respiration. These nasal masks typically receive a gas supply line which delivers gas into a chamber formed by walls of the mask. The walls usually are semi-rigid and have a face contacting portion including an aperture which is aligned with the wearer's nostrils. The face contacting portion can comprise a soft, resilient elastomeric material which may conform to various facial contours. The mask normally is secured to the wearer's head by straps. The straps are adjusted to pull the mask against the face with sufficient force to achieve a gas tight seal between the mask and the wearer's face. Gas is thus delivered to the mask and through the aperture to the wearer's nasal passages.

Problems often arise with masks of the above configuration. For example, the mask may be dislodged, thereby breaking the seal between the mask and wearer. This may occur if the wearer rolls over when sleeping thereby creating a drag force on the gas supply line which is transmitted to the mask, breaking the seal. In the case of a mask being used for the administration of Continuous Positive Airway Pressure (CPAP) treatment for the condition obstructive sleep apnea, such a leak can result in the pressure supplied to the entrance of the wearer's airway being below the therapeutic value, and the treatment becoming ineffective.

Another problem is that the face contacting portion may apply excessive pressure to the wearer's face resulting in discomfort and possibly skin irritation. This can occur because the face contacting portion has to distort beyond its normal range of elasticity to conform to certain facial contours which requires the application of excessive forces. In some cases these excessive pressures and forces may cause the face to distort to conform with the face contacting portion to increase wearer discomfort, facial soreness and ulceration.

Other types of devices exist whereby small nostril nosepieces (pillows) are held in place by a harness strapped over the wearer's head, for example as shown in prior art U.S. Pat. No. 4,782,832 (Trimble et al). While this arrangement may alleviate some problems regarding seal breakage and skin abrasion, the harnesses associated with such devices are quite cumbersome for the wearer, as are the gas supply lines. Also, air 'jetting' into the nostrils can be irritating to the patient making such devices generally uncomfortable to use.

A further example of the prior art also is disclosed in U.S. Pat. No. 5,243,971 (Sullivan et al).

Cushion masks have also been developed. These cushion masks have an inflated cushion which provides comfort to the wearer. However, these masks, under certain circumstances, may form a tuck or pucker resulting in a leak.

It is an object of the invention to overcome or at least substantially ameliorate one or more of the foregoing disadvantages.

SUMMARY OF THE INVENTION

In one broad form, the invention discloses a nasal mask cushion to sealingly connect a mask to a wearer's face, the cushion comprising:

a substantially triangularly-shaped frame of resilient material having a rim to surround wearer's nose;

a membrane also of resilient material, said membrane being relatively more flexible than said frame, and being of the same general shape as said rim and fixed to and extending away from said frame so as to have an outer surface spaced from said rim, a portion of said outer surface forming a face contacting seal; and a nose-receiving cavity bounded by said frame and said membrane;

and wherein said seal portion is generally coterminous with respect to said rim and is resiliently deformable towards said rim in use of said cushion.

In one particularly advantageous form, the membrane is substantially saddle-shaped. The membrane further has a centrally located aperture through which the wearer's nose passes to enter said cavity.

It is preferred that the cushion and membrane each include a co-located notch to accommodate the bridge of the nose of the wearer. Typically, the seal portion contacts at least the wearer's nose, and preferably, also the facial tissue around the sides and over the bridge of the nose and between the base of the nose and the top lip.

The invention further discloses a nasal mask for connection to a wearer's face comprising:

a mask body for connection with a supply of breathable gas; and a nasal cushion, the body and cushion defining a nose-receiving cavity, said cushion including:

a substantially triangularly-shaped frame of resilient material having a rim to surround said wearer's nose;

a membrane also of resilient material, said membrane being relatively more flexible than said frame, and being of the same general shape as said rim and fixed to and extending away from said frame so as to have an outer surface spaced from said frame, a portion of said outer surface forming a face contacting seal;

and wherein said seal portion is generally coterminous with respect to said rim and is resiliently deformable towards said rim in use of said mask.

The mask body can further include attachment points from which securing straps can be attached, and by which the mask can be secured to the wearer's head. The nasal mask can yet further comprise an arm depending from said body from which a further securing strap(s) can be attached.

The invention further discloses nasal CPAP treatment apparatus comprising a flow generator for the supply of gas at a pressure elevated above atmospheric pressure to a gas delivery conduit, the conduit in turn coupled to a nasal mask as described immediately above.

In one particularly preferred form, a supply of gas can be provided to said cavity, said supply of gas assisting, but not solely causing maintenance of a seal by said seal forming portion of said membrane to the face of the wearer in use of the cushion.

Advantageously, the membrane and the rim are substantially shaped to the facial contour, and the membrane does not need to turn in on itself thus contacting the face without folds or creases. With the cushion/mask secured to the wearer's head, the headstraps need only to be tensioned to balance the force due to mask gas pressure that tends to lift the mask off the face. Such relatively lower mask-to-face pressure results in greater patient comfort, and a reduction in the likelihood of skin irritation.

BRIEF DESCRIPTION OF THE DRAWINGS

An embodiment of the invention will now be described with reference to the accompanying drawings, in which:

FIG. 5 is a side view of the mask cushion;

FIG. 6 is a front view of the mask cushion;

FIG. 7 is a rear view of the mask cushion;

FIG. 8 is a sectional view along section lines 8—8 of FIG. 7; and

FIG. 9 is a sectional view along section lines 9—9 of FIG. 7.

DETAILED DESCRIPTION OF THE PREFERRED EMBODIMENTS

Figure 1:
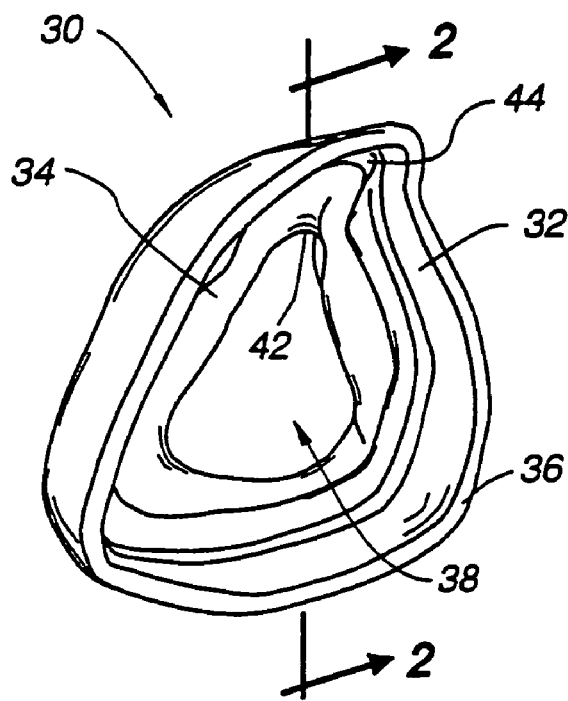
FIG. 1 is a rear perspective view of a mask cushion embodying the present invention.
Figure 2:
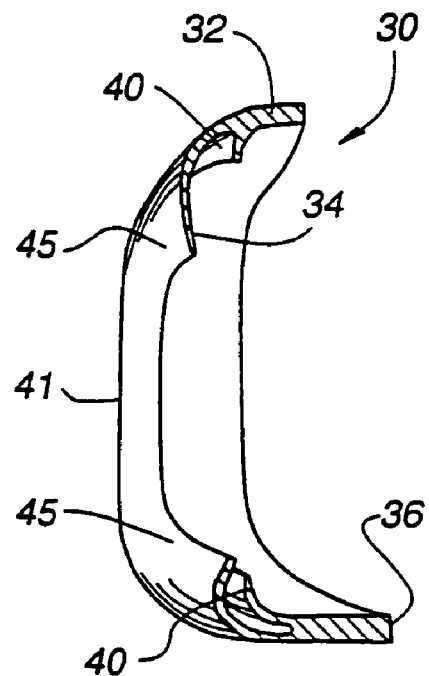
FIG. 2 is a cross-sectional view along line 2—2.

FIG. 1 shows a perspective view of a nasal cushion 30 embodying the invention. FIG. 2 shows the cross-sectional view along line 2—2. Referring to FIGS. 1–2 and 5–9, the cushion 30 comprises a substantially triangularly shaped frame 32 from which extends a membrane 34. The frame 32 has a scalloped edge 36 by which the cushion 30 is affixed to a mask body, as presently will be described.

The membrane 34 has an aperture 38 into which the wearer's nose is received in use of the cushion 30. The membrane 34 is spaced away from the rim 40 of the frame 32, and its outer surface 41 is of substantially the same shape as the rim 40. The outer surface 41 of the membrane 34 and the rim 40 of the frame 32 also can be described as generally saddle shaped. The shaping of the outer surface 41 of the membrane 34 and the rim 40 of the frame 32 also include respective notches 42,44 that receive the bridge of the wearer's nose in use of the cushion 30.

As is best seen in FIG. 2, the frame 32 and the membrane 34 are integrally formed, typically by in a one-shot molding process. The frame 32 and the membrane 34 are fabricated from a resilient material. One suitable such material is SILASTIC™ silicone elastomer manufactured by Dow Coming. The frame 32, is one preferred embodiment, has a typical thickness at its rim 40 of 1.5 mm. The membrane 34, in a preferred embodiment, has a typical thickness of 0.35 mm. In this way, the membrane 34 is relatively more flexible than the rim 40.

In use of the cushion 30, a wearer's nose will be inserted in the aperture 38 to engage a seal forming portion 45 (formed between the dashed lines of FIG. 3) of the outer surface 41 to cause deformation of the membrane 34. Depending upon the securing force supplied to the membrane 34, it may deform to a point where it butts against the rim 40 of the frame 32. The frame 32 has a rigidity sufficient to withstand usual securing pressures in use of the cushion 30 to tend to retain its shape and resist deformation. It thus acts as a supporting structure.

Figure 3:
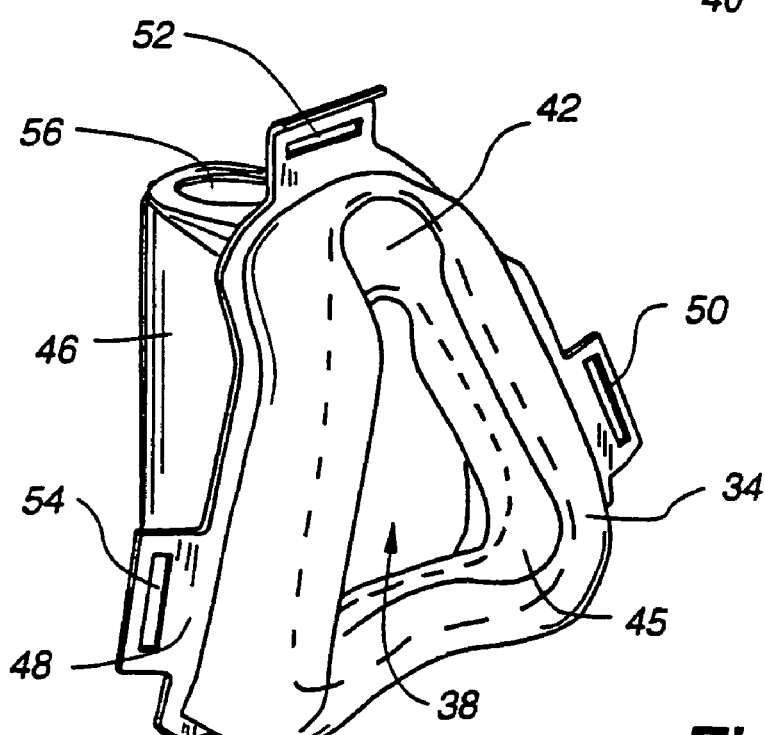
FIG. 3 is a perspective view of a nasal mask including the cushion of FIGS. 1 and 2.

Referring now to FIG. 3, the nasal cushion 30 is shown attached to a mask body 46 by the edge 36 of the frame 32, adhered or otherwise secured to a flange 48 of the mask body 46. Only the outer surface 41 of the membrane 34 can be seen. The flange 48 includes three slots 50, 52, 54 from which tensioning straps can be attached to secure the cushion 30 and the mask body 46 (in combination) to the head of the wearer.

The mask body 46 forms a cavity that can receive the nose of the wearer by the aperture 38. A port 56 is provided at the top of the mask body 46 by which breathable gas can be supplied to the chamber.

Figure 4:
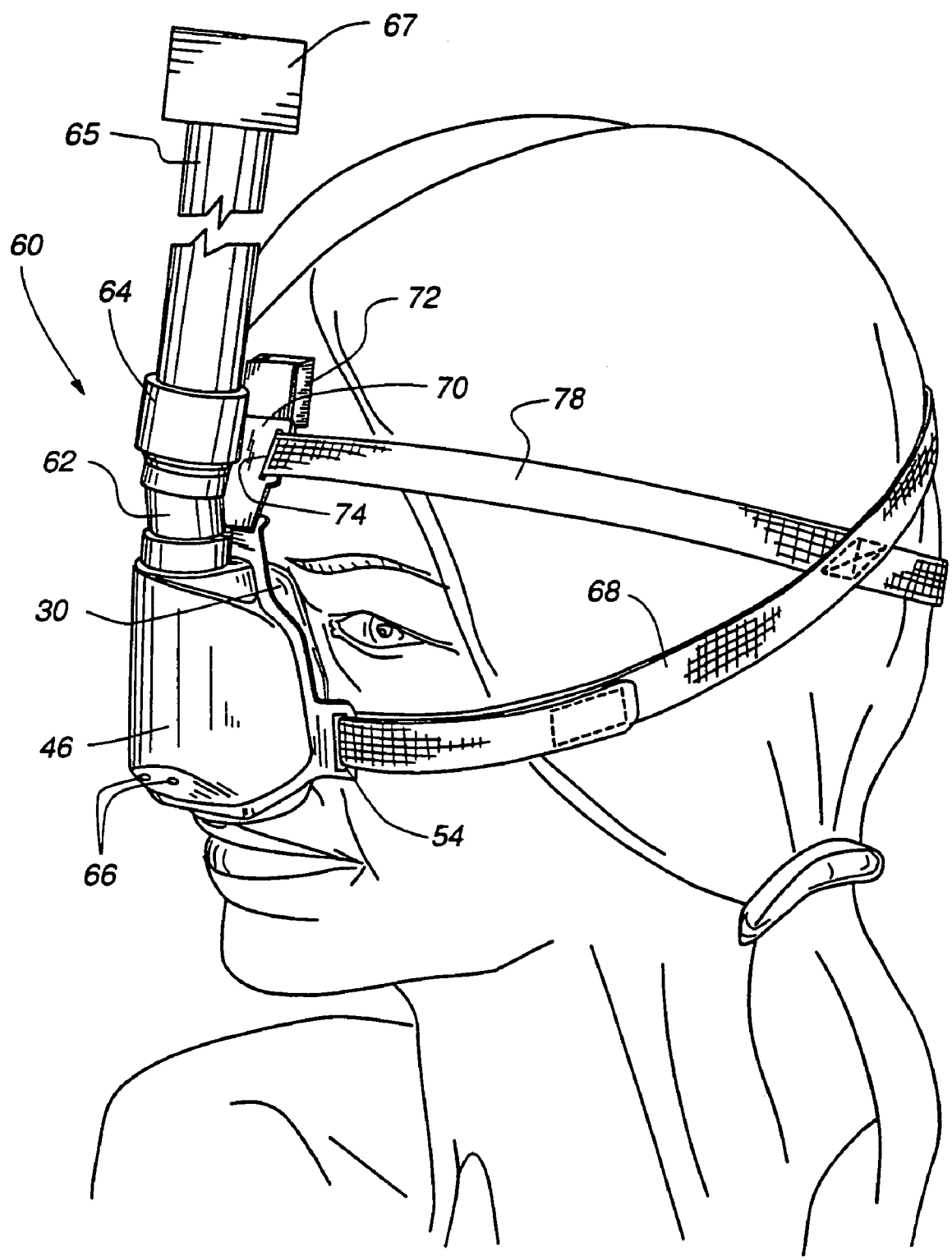
FIG. 4 is a perspective view of the nasal mask of FIG. 3 secured to a wearer's head.

Referring now to FIG. 4, there is shown a nasal mask 60 including the mask body 46 and the mask cushion 30. A coupling tube 62 is connected at one end with the inlet port 56, and at the other to a socket 64 into which can be received a gas delivery tube 65 for the supply of breathable gas to the chamber internal of the mask body 46. The mask body 46 from a flow generator 67 also has two vent openings 66 by which expired gas is exhausted. A first fastening strap 68 is fixed between to the lower two slots 50, 54. The upper slot 52 receives an arm 70, the top end of which has a resilient pad 72 to engage the forehead of the wearer. The arm 70 has two slots 74 (only one slot shown in FIG. 4) along its side edges, by which a second fastening strap 78 is secured.

In fitting the nasal mask 60, the wearer's nose is received through the aperture 38 into the chamber within the mask body 46. The seal forming portion 45 thus contacts both the surface of the wearer's nose and a portion of the wearer's face in the region between the base of the nose and the upper lip, and around the sides and over the bridge of the nose. The shape of the seal forming portion 45 is particularly suited to effectively seal the difficult region of the facial contour that is the crease between the sides of the nose and the face. Depending upon the tension applied by the fastening straps 68,78, a seal is formed with the membrane 34 remaining spaced from the rim 40 of the cushion frame 32. While the provision of pressurised gas to the chamber of the mask body 46 assists in the maintenance of a seal between the membrane 34 and the wearer's nose and face, it is not essential in most cases, and an effective seal will be formed absent any such pressurised gas. On relative movement of the mask 60 in relation to the wearer's head, the nose will be restrained by contacting the frame 32. Thus only limited relative motion between the mask 60 and the wearer's nose and face occurs.

The membrane 34 closely imitates the facial contour, and because of its relatively lesser stiffness than the frame 32, can conform to particular facial structures with minimum force, and without a tendency to fold or crease.

If the fastening strap 68, 78 are tensioned to excess, the membrane 34 deforms to abut the rim 40 of the cushion 32, the frame 32 thus acting as an "end limit". In such a configuration, almost zero relative movement can occur between the mask 60 and the wearer's head.

The nasal cushion 30 and nasal mask 60 has been described with reference to CPAP or assisted respiration treatment, however it is to be understood that the invention generally is applicable to any application where gas and/or atomized liquid is to be supplied to the entrance of the nasal airways. Such applications include nebulisers, gas masks and anaesthetic machines.

We claim:

1. A mask cushion to sealingly connect a mask to a wearer's face, the cushion comprising:
   a nasal bridge region, a cheek region and a lower region below the cheek region;
   a substantially triangularly-shaped frame of resilient material having a first molded inwardly curved rim; and
   a membrane of resilient material, said membrane being thinner and more flexible than said first rim, said membrane having a second molded inwardly curved rim, said second rim spaced a distance from said first rim, said distance grater than a thickness of the first rim, said distance measured when the mask is not in use, a portion of said second rim forming a face contacting seal,
   wherein the membrane has a thickness of about 0.35 mm and the rim has a thickness of about 1.5 mm.

2. The mask cushion of claim 1, wherein the membrane is conformable, in use, to various facial structures with minimum force.

3. The mask cushion of claim 2, wherein a maximum deformation position of the membrane is defined by the rim.

4. The mask cushion of claim 3, wherein the maximum deformation position is not reached under normal tightening force of the mask to the wearer's face.

5. The mask cushion of claim 1, wherein the frame, membrane and rim are formed as a one-piece unit.

6. A mask for connection to a wearer's face comprising:
   a mask body for connection with a supply of breathable gas; and
   a cushion secured to said mask body, the body and cushion forming a nose-receiving cavity, said cushion including:
      a nasal bridge region, a cheek region and a lower region;
      a substantially triangularly-shaped frame of resilient material having a molded inwardly curved rim; and
      a membrane also of resilient material, said membrane being relatively more flexible than said rim, said membrane and rim, in cross-section, being generally curved away from the wearer in use, said membrane arranged to generally cover the rim and being spaced a distance from an outer surface of said rim at least in one of the bridge region, the cheek region or the lower region, said distance greater than a thickness of the rim, said distance measured when the mask is not in use, a portion of said membrane forming a face contacting seal;
      wherein said seal portion is resiliently deformable towards said rim in use of said mask.

7. The mask of claim 6, further comprising an arm coupled to and extending above the nasal bridge region of the mask, the arm including an oblong slot to receive a strap.

8. The mask of claim 7, further comprising a single resilient pad mounted on the arm and centered above the nasal bridge region of the mask.

9. The mask of claim 6, wherein the membrane is conformable, in use, to various facial structures with minimum force.

10. The mask of claim 9, wherein a maximum deformation position of the membrane is defined by the rim.

11. The mask of claim 10, wherein the maximum deformation position is not reached under normal tightening force of the mask to the wearer's face.

12. The mask of claim 6, wherein the frame, membrane and rim are formed as a one-piece unit.

13. The mask of claim 6, wherein the rim is at least twice as thick as the membrane.

14. The mask of claim 6, wherein each and every portion of the rim is covered by the membrane.

15. A mask for connection to a wearer's face comprising:
    a mask body for connection with a supply of breathable gas; and
    a cushion secured to said mask body, the body and cushion forming a cavity, said cushion including:
       a frame of resilient material having a molded inwardly curved rim; and
       a membrane also of resilient material, said membrane being relatively more flexible than said rim, said membrane and rim, in cross-section, being generally curved so that the membrane presents a generally convex surface to the wearer's face in use, said membrane arranged to generally cover the rim and at least a portion of the membrane being spaced a distance from an outer surface of said rim, said distance greater than a thickness of the rim, said distance measured when the mask is not in use, a portion of said membrane forming a face contacting seal;
       wherein said seal portion is resiliently deformable towards said rim in use of said mask, and
       wherein the mask body includes a strap attachment point on each lateral side thereof.

16. The mask of claim 15, wherein the frame, membrane and rim are formed as a one-piece unit.

17. The mask of claim 16, wherein the membrane is conformable, in use, to various facial structures with minimum force.

18. The mask of claim 17, wherein a maximum deformation position of the membrane is defined by the rim.

19. The mask of claim 18, wherein the maximum deformation position is not reached under normal tightening force of the mask to the wearer's face.

20. The mask of claim 16, wherein the rim is thicker than the membrane.

21. The mask of claim 20, wherein the rim is at least twice as thick as the membrane.

22. The mask of claim 21, wherein the rim has a thickness of about 1.5 mm and the membrane has a thickness of about 0.35 mm.

23. The mask of claim 21, wherein the membrane and the rim have a common general shape.

24. The mask of claim 16, wherein an outer surface of the membrane is substantially saddle shaped.

25. The mask of claim 16, wherein the membrane has an aperture that is smaller than an aperture of the rim.

26. The mask of claim 25, wherein the mask body includes a port by which pressurized breathable gas may be supplied to the cavity.

27. The mask of claim 26, wherein the mask body includes at least two vent openings for washout of expired gas.

28. The mask of claim 15, wherein each and every portion of the rim is covered by the membrane.

29. A CPAP apparatus for treatment of sleep disordered breathing comprising:
    a flow generator to supply gas at a pressure elevated above atmospheric;
    a gas delivery conduit coupled between said flow generator and the mask of claim 15.

* * * * *